(12) United States Patent
Rehrl et al.

(10) Patent No.: US 6,230,607 B1
(45) Date of Patent: May 15, 2001

(54) ADJUSTING DEVICE FOR A PNEUMATIC DRIVE, PARTICULARLY FOR A MEDICAL OR DENTAL INSTRUMENT

(75) Inventors: Gregor Rehrl, Oberndorf; Richard Kardeis, Bürmoos; Wilhelm Brugger, Bergheim bei Salzburg, all of (AT)

(73) Assignee: Dentalwerk Bürmoos Gesellschaft m.b.H., Bürmoos (AT)

( * ) Notice: Subject to any disclaimer, the term of this patent is extended or adjusted under 35 U.S.C. 154(b) by 0 days.

(21) Appl. No.: 09/315,686

(22) Filed: May 20, 1999

(30) Foreign Application Priority Data

May 20, 1998 (AT) ........................................................ 873/98

(51) Int. Cl.⁷ ................ F15B 11/08; F16K 5/10
(52) U.S. Cl. ..................... 91/418; 251/208; 251/344; 251/345
(58) Field of Search ................ 91/418, 428; 251/208, 251/297, 344, 345

(56) References Cited

U.S. PATENT DOCUMENTS

| | | | | |
|---|---|---|---|---|
| 2,911,008 | * | 11/1959 | Du Bois | 251/208 X |
| 3,033,226 | * | 5/1962 | Allen | 251/344 X |
| 5,123,449 | * | 6/1992 | Nowicki | 251/208 X |
| 5,148,830 | * | 9/1992 | Liu | 251/344 X |
| 5,332,194 | * | 7/1994 | Austin, Jr. et al. | 251/345 |
| 5,782,455 | * | 7/1998 | Burnworth | 251/345 |

FOREIGN PATENT DOCUMENTS 9217943   7/1993   (DE).
96/14024  5/1996   (WO).

* cited by examiner

Primary Examiner—John E. Ryznic
(74) Attorney, Agent, or Firm—Friedrich Kueffner

(57) ABSTRACT

An adjusting device for a pneumatic drive, particularly a pneumatic drive of a medical or dental instrument, for example, a handpiece or angle piece, which delivers its energy by vibration and in which the vibrations are produced by a pneumatic drive, wherein an air flow is controlled by having an air supply line and an air discharge line end at a distance from each other at a surface and by providing a counter-surface which is movable relative to the surface and, which, in dependence of its position relative to the surface, forms a flow path with a defined flow resistance between the air supply line and the air discharge line.

3 Claims, 2 Drawing Sheets

ADJUSTING DEVICE FOR A PNEUMATIC DRIVE, PARTICULARLY FOR A MEDICAL OR DENTAL INSTRUMENT

BACKGROUND OF THE INVENTION

1. Field of the Invention

The present invention relates to an adjusting device for a pneumatic drive, particularly a pneumatic drive of a medical or dental instrument, for example, a handpiece or angle piece, which delivers its energy by vibration and in which the vibrations are produced by a pneumatic drive.

2. Description of the Related Art

In the past, pneumatically driven vibration systems have been offered by only two companies who own the corresponding patents. The manufacturers of instruments obtain these systems from the two companies and, until recently, mounted them exclusively in so-called scalers which are devices for removing tartar.

In the year 1992, it was recognized that it is possible by means of such vibrating tools with appropriately configured tool surfaces (covered with diamond chips, etc.) to also remove teeth or bones or other hard materials. This was disclosed in DEG 92 17 943.6 U1.

A further development of this concept is disclosed in WO96/14024A. A shaping tool is placed on such a conventional scaler with produces in a tooth a negative shape of the tool. The removal of the material is effected by the oscillations of the shaping tool and, thus, the size of the removed area is essentially larger than the tool by an extent which corresponds to this oscillation amplitude. Since the oscillation amplitude is extremely small, recesses are formed which are dimensionally very accurate, which may be defined by sharp edges and which significantly deviate from the round cross-section.

These types of recesses in a tooth are required for prefabricated tooth replacement materials which are standardized with respect to shape, such as inlays. The replacement materials have at the appropriate locations precisely formed and shaped projections which fit into the recesses produced in the above-described manner and are glued or cemented into the recesses.

Other applications relate to the root canal treatment and the cleaning of the tooth surface with oscillating brushes. For carrying out these treatments, it is also possible to use instruments which have a pneumatic drive. Of course, air flows for other apparatus and devices also require a control, usually within wide limits; however, the control still has to be sensitive.

It has now been found that the material removal capacities and the oscillation amplitudes vary substantially in one and the same instrument in dependence on the tool placed on the drive. We have found that the reason for this is the fact that the oscillation behavior of the tool, the tool shaft and the pneumatic vibration drive forms a complicated oscillation system and the maximum material removal capacity and dimensional accuracy of the formed recess in various tools or applications are due to the respectively different air flows to the pneumatic vibration drive.

Therefore, the present invention relates to an adjusting device for a pneumatic vibration drive in a dental or medical instrument of the above-described type.

An adjusting device of this type is used in practice and is composed of an adjusting sleeve arranged on the handpiece, wherein a rotation of the adjusting sleeve causes a Teflon block to close the drive air line to a different extent. This control is extremely inaccurate and not linear.

A later adjusting device by the same manufacturer, wherein the configuration thereof is unknown, includes an adjusting sleeve which can be rotated by approximately four full rotations relative to the center axis of the handpiece for moving the sleeve between the position fully closed and the position fully open. However, this adjusting device is completely useless for the purpose of the present invention because the physician using the adjusting device cannot determine the present position of the adjusting device; this determination cannot even be made when the instrument is idling in the air because the oscillation behavior of the above-described oscillating system in the unloaded state differs significantly or may differ from the behavior in the loaded state and even an experienced user cannot find any indication concerning the adjustment of the adjusting device.

Moreover, the device known in the art is in spite of a large adjusting distance entirely incapable of exhibiting an even approximate linear behavior, so that there are adjusting ranges in which even a small rotation of the adjusting sleeve results in a substantial change of the air flow, while in another range even a substantial rotation of the adjusting sleeve produces only a slight change of the air flowing through.

SUMMARY OF THE INVENTION

Consequently, it is the object of the present invention to provide an adjusting device in which the disadvantages of the previously known adjusting devices are eliminated and which is capable of indicating clearly to the user prior to the start of operation of the instrument in a clear and simple manner the position of the adjusting device.

In accordance with the present invention, an air flow is controlled by having an air supply line and an air discharge line end at a distance from each other at a surface and by providing a counter-surface which is movable relative to the surface and, which, in dependence of its position relative to the surface, forms a flow path with a defined flow resistance between the air supply line and the air discharge line.

More specifically, the above-described object is met in a device of the above-described type in that the adjusting device is composed of an adjusting ring rotatably mounted on the handpiece, wherein the adjusting ring is rotatable by less then 360° about the axis of the handpiece. The adjusting ring has at its essentially circular cylindrical inner wall surface a recess which has a continuously changing cross-section in the circumferential direction. At least one drive air supply line extends in the handpiece essentially radially outwardly and a drive air transfer line extends in the handpiece essentially radially inwardly starting from the inner wall surface of the adjusting ring toward the air-driven vibration drive, wherein, depending on the angular position of the adjusting ring relative to the handpiece, the recess of the adjusting ring is located to a greater or lesser extent opposite the end of the air supply line and/or opposite the end of the air discharge line.

As a result of the configuration according to the present invention, it is achieved that based on its angular position the adjusting ring provides a clear indication of the adjustment of the adjusting device; this can be made even clearer by providing appropriate markings at the adjusting ring and at the handpiece body.

In accordance with a further development of the invention, several markings may be provided which serve as indications for the user for the respectively best adjustment for a predetermined manner of operation.

In accordance with another feature, it is also possible to find particularly important positions more easily by a conventional locking mechanism, so that reaching of the correct position can be heard or felt.

The various features of novelty which characterize the invention are pointed out with particularity in the claims annexed to and forming a part of the disclosure. For a better understanding of the invention, its operating advantages, specific objects attained by its use, reference should be had to the drawing and descriptive matter in which there are illustrated and described preferred embodiments of the invention.

DESCRIPTION OF THE PREFERRED EMBODIMENTS

Figure 1:
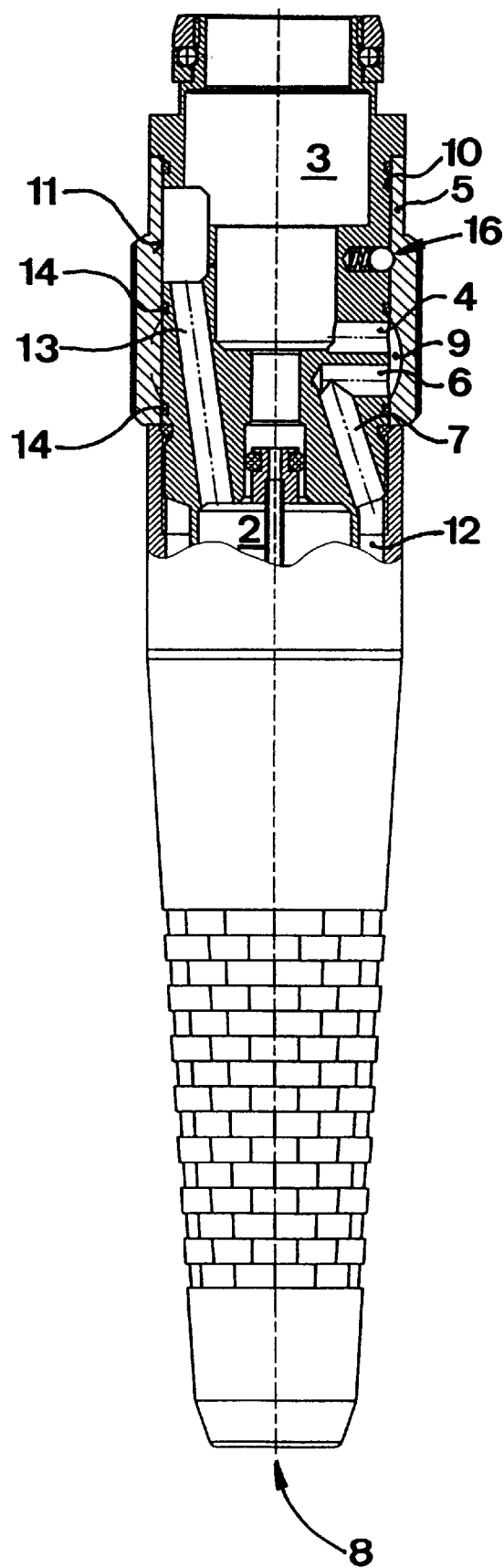
FIG. 1 is an axial sectional view of a handpiece according to the present invention.

As illustrated in FIG. 1, a handpiece 1 according to the present invention includes a conventional pneumatic vibration drive 2 which causes a tool holder 8 to oscillate at a high frequency. The air is supplied to the handpiece 1 through a conventional supply hose, not shown, and a coupling, also not shown, which can be inserted into the interior 3 of the handpiece 1.

The drive air is then conducted through an essentially radially extending bore 4, which ends at the outer circumferential surface 10 of the body of the handpiece 1, into an area which is located opposite the inner wall surface 11 of the adjusting ring 5.

An air transfer line 6 extends essentially radially at a distance from the end of the air supply line 4, starting from the circumferential surface 10 to a further air line 7 through which the drive air finally reaches an annular space 12 which surrounds the pneumatic vibration drive 2. Nozzle-like openings lead from this annular space 12 into the interior of the drive and cause the drive to be driven. The discharge air is once again conducted through an air discharge line 13 into the interior 3 of the handpiece 1 and is discharged through the supply hose.

When the coupling is engaged, the recess 3 is divided by sealing members, usually O-rings, into individual portions at the coupling shaft, so that the drive air and the return air are kept separate from each other. The adjusting ring 5 is sealed relative to the body of the handpiece 1 in a similar manner by means of O-ring seals 14.

FIG. 1 additionally shows a conventional ball locking device 16 which makes it possible to easily and precisely reach adjustment positions which are needed particularly frequently or which must be adhered to precisely, and which secures the adjustment positions against undesired rotation. This locking device is composed of a spring-biased ball in the instrument body 15 which is received in one spherical recess or alternatingly in various spherical recesses in the adjusting ring 5 and secures in a positively engaging manner the position of the two components relative to each other.

Figure 2:
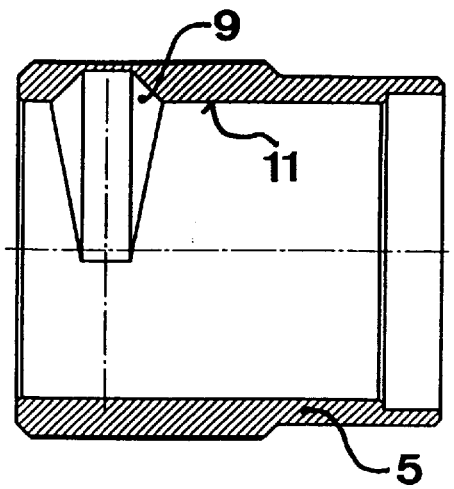
FIG. 2 is a sectional view, on a larger scale, of an adjusting ring according to the present invention.

FIG. 2 shows the adjusting ring 5 on a larger scale. FIG. 2 clearly shows the recess 9 on the inner wall surface 11 which is otherwise circular cylindrical. The ends of the air lines 4 and 6 are arranged in such a way that, when the adjusting ring 5 is in its angular position corresponding to completely opening the lines, the ends of the air lines 4 and 6 are located with their entire cross-sections within the area of the recess 9 and, thus, permit a maximum flow of air.

When the ring 5 is increasingly rotated from this position toward the closed position, continuously and progressively larger and larger areas of the cross-sections of the air lines 4 and 6 are moved out of the area of the recess 9 and are located diametrically opposite the circular cylindrical inner wall surface 11 of the adjusting ring 5 until at least one, preferably both ends, of the air lines 4 and 6 are located opposite the circular cylindrical inner wall surface 11 and, in accordance with a particularly preferred feature, are located at a distance from the recess 9.

The inner wall surface 11 and the outer circumferential surface 10 of the body 15 of the handpiece 1 necessarily are spaced apart from each other by a very small distance which is required to facilitate rotation and to take into consideration the manufacturing tolerances, however, this distance is so small that it does not permit any perceivable air flow, so that, when the adjusting ring 5 has been rotated into its angular position corresponding to a completely closed position, the ends of the two air lines 4 and 6 are located completely opposite the circular cylindrical inner wall surface 11 and no flow is possible between the lines 4 and 6.

Figure 3:
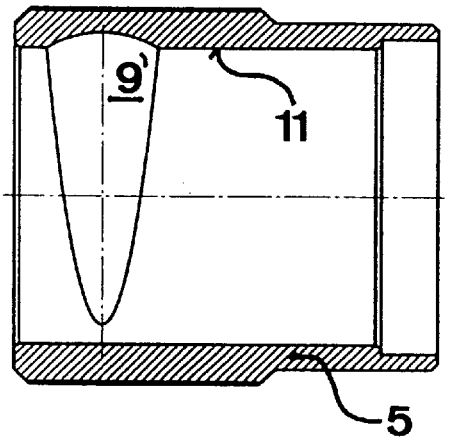
FIGS. 3 and 4 are sectional views of additional embodiments of the adjusting ring.

FIG. 3 of the drawing shows an adjusting ring 5 whose recess 9' has a rounded shape, while the recess 9 shown in FIG. 2 has a linear surface as well as a depth which increases linearly with the circumference.

Figure 4:
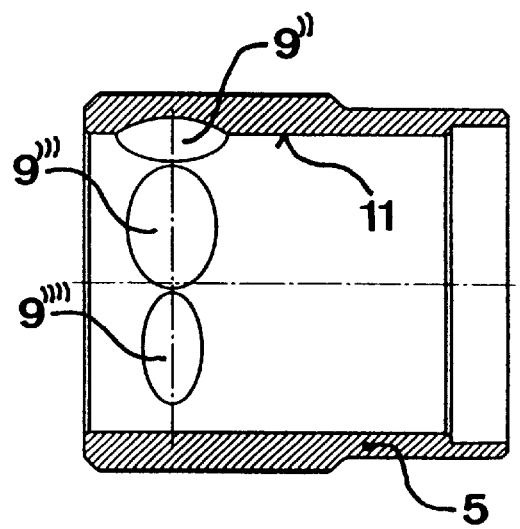

FIG. 4 shows an embodiment in which a plurality of predetermined positions are provided; the combination with a ball locking unit is particularly recommended in this embodiment. The individual recesses 9', 9''' and 9'''' each have a predetermined flow resistance and correspond to discrete adjustment positions in this manner. While this does not make possible a continuous adjustment, this embodiment makes possible particularly accurate individual adjustments.

Of course, the shapes of the individual recesses 9''–9'''' can also be constructed differently, particularly essentially linear grooves can be used which can be easily produced by milling cutting. In these cases, the adjusting effect is not produced by the differing overlap of the ends of the air lines 4, 6, but also or exclusively by the flow resistance of the recesses.

Consequently, the adjusting device according to the present invention in principle is composed of an adjusting ring 5 which at its inner wall surface 11 has at least one recess 9 through which the two air lines 4, 6 of the instruments can be connected with different flow resistances and the air flow can be adjusted to desired values.

The present invention can be used in all cases where a gas flow has to be adjusted and where this adjustment has to be carried out simply and so as to be easily recognizable. Particularly suitable is the device for applications in which the gas source has constant parameters (pressure, temperature) because always the same gas flows correspond to the intended points of operation.

In view of the present invention, those skilled in the art of flow technology will have no problem finding variations and embodiments of the invention, without leaving the basic concept thereof. For example, the unavoidable gap between the surface and counter-surface can be sealed by means of sealing elements, for example, O-rings, the ends of the gas lines in the surface can be configured differently or the line or lines can end in a plurality of openings.

The surface and the counter-surface may have different shapes and may be moved toward each other in different manners. Preferred are a rotational movement when the surface is circular cylindrical, or a translatory movement along a generatrix of the surface. A combined rotary and lifting movement is also conceivable, although this appears to be not economical for reasons of manufacturing technology.

While specific embodiments of the invention have been shown and described in detail to illustrate the inventive principles, it will be understood that the invention may be embodied otherwise without departing from such principles.

We claim:

1. An adjusting device for a pneumatic drive of a medical or dental instrument, wherein the instrument delivers energy by vibration and the vibrations are produced by a pneumatic drive, the adjusting device comprising an adjusting ring rotatably mounted on the instrument, wherein the adjusting ring is adjustable within a range of less than 360°, the adjusting ring having an essentially circular cylindrical inner wall surface, wherein the inner wall surface has at least two separate recesses, wherein at least one drive air supply line extends in the instrument essentially radially outwardly and ends at an outer wall surface of the instrument, further comprising at least one drive air transfer line in the instrument extending from the outer wall surface of the instrument essentially radially inwardly toward the pneumatic drive, wherein, depending on an angular position of the adjusting ring, either none or one of the recesses are located at least partially opposite an end of the drive air supply line and an end of the drive air transfer line.

2. The adjusting device according to claim 1, further comprising a positioning device for securing in a frictionally engaging manner one or more positions of operation of the adjusting ring relative to the instrument.

3. The adjusting device according to claim 2, wherein the positioning device is comprised of a ball-type locking means.

* * * * *